United States Patent [19]
Yoshiyama et al.

[11] Patent Number: 6,078,385
[45] Date of Patent: Jun. 20, 2000

[54] METHOD OF INSPECTING MAGNETIC DISC AND APPARATUS THEREFOR AND PROCESS FOR PRODUCING THE MAGNETIC DISC

[75] Inventors: Ryuichi Yoshiyama; Takashi Yamauchi, both of Yokohama, Japan

[73] Assignee: Mitsubishi Chemical Corporation, Tokyo, Japan

[21] Appl. No.: 09/018,155

[22] Filed: Feb. 3, 1998

[30] Foreign Application Priority Data

Feb. 3, 1997 [JP] Japan ................................. 9-020297

[51] Int. Cl.⁷ .................................................. G01N 21/00
[52] U.S. Cl. ...................... 356/237.1; 356/239.1
[58] Field of Search ................ 356/237.1–237.5, 356/73, 239.1–239.8, 445, 382; 250/559.45, 559.46; 369/58, 54

[56] References Cited

U.S. PATENT DOCUMENTS 4,865,445  9/1989  Kuriyama et al. ......................... 356/73
5,646,415  7/1997  Yanagisawa ............................ 356/430

FOREIGN PATENT DOCUMENTS

| 63-1532 | 1/1988 | Japan . |
| 6-14014 | 2/1994 | Japan . |
| 2531293 | 11/1996 | Japan . |
| 62-267650 | 11/1997 | Japan . |

*Primary Examiner*—Frank G. Font
*Assistant Examiner*—Tu T. Nguyen
*Attorney, Agent, or Firm*—Dike, Bronstein, Roberts & Cushman, LLP; David G. Conlin; William J. Daley, Jr.

[57] ABSTRACT

The present invention relates to a method of inspecting a magnetic disc, comprising:

optically inspecting a surface of said magnetic disc to detect defects thereon; and conducting a magnetic defect inspection to an area which is smaller than said optically inspected surface and including the optically detected defective portions and vicinities thereof.

19 Claims, 3 Drawing Sheets

METHOD OF INSPECTING MAGNETIC DISC AND APPARATUS THEREFOR AND PROCESS FOR PRODUCING THE MAGNETIC DISC

BACKGROUND OF THE INVENTION

The present invention relates to a method of inspecting a magnetic disc and an apparatus therefor. More particularly, the present invention relates to a method of inspecting a magnetic disc, which comprises an optically inspecting step and a magnetic inspecting step.

Conventionally, the inspection of magnetic discs has been conducted in such a manner that signals are written thereon and then read out therefrom by a magnetic head, thereby detecting defective portions having a larger change in signal output relative to the average signal output level.

Specifically, by using a magnetic inspection apparatus for magnetic discs as shown in FIG. 2 (generally called "certifier"), given signals are recorded on a magnetic disc 1 and then reproduced therefrom by a magnetic head 2 having a signal processing unit 11 to examine signal output levels, whereby portions from which the signal outputs beyond a certain threshold value are generated, are detected as defects.

However, in association with recent increase in storage capacity and track density of magnetic discs, there arises a problem that the conventional inspection method requires too much time to inspect such magnetic discs, resulting in deterioration in the productivity thereof. Consequently, in order to shorten the inspection time in the magnetic inspection method, there has been proposed a method of inspecting tracks on the magnetic disc in a track-skipping or jumping manner.

However, if the magnetic disc are magnetically inspected in such a track-skipping or jumping manner, there arises such a problem that defects on the tracks located in regions excluded from the inspection can be no longer detected. In the case where the sizes of defects on a magnetic disc are smaller than a predetermined size and the number of the defects is smaller than a predetermined number, the defects on the magnetic disc can be corrected by error correction processing at a disc drive, thereby rendering the magnetic disc usable. However, in the case where such defects whose lengths are larger than a predetermined value are located on the same tracks, the error correction processing is no longer effective. As a result, the magnetic disc having such larger defects must be rejected as a defective disc. The smaller defects are distributed uniformly to some extent on the surface of the magnetic disc. Therefore, even when the tracks of the magnetic disc are inspected by the a track-skipping or jumping manner, the number of the smaller defects can be estimated from an area ratio between inspected regions and skipped or jumped non-inspected regions. However, in the case where the larger defects are located on the same tracks, the number thereof cannot be estimated unlike the smaller defects. In consequence, in order to avoid these problems, optical inspection methods have been used.

As the optical inspection methods, there have been exemplified a light scattering method, a laser Doppler method, a laser interference method or the like. The inspection according to the light scattering method has been conducted in the following manner. As shown in FIG. 3, the inspection apparatus used in this method comprises a light source 3 for irradiating light onto the surface of the magnetic disc 1, a first light-receiving unit 4 for receiving a low-angle scattered light and a second light-receiving unit 6 for receiving a scattered light coming through a shield plate 5 in the mirror reflection direction. By using the inspection apparatus, when the scattered light measured in the mirror reflection direction or vicinities thereof has a predetermined light intensity or higher and the detection is continued for a predetermined period of time or longer and when the low-angle scattered light has a predetermined light intensity or lower, it can be judged that defects are detected at the inspected positions on the magnetic disc. On the other hand, when the low-angle scattered light has a light intensity of more than the predetermined value, it can be judged that dusts or other foreign substances exist on the inspected positions on the magnetic disc, thereby distinguishing the detection of dusts from that of the defects.

However, as a result of the present inventors' studies, it has been found that the defects detected by the optical inspection method have not necessarily been consistent with those detected by the magnetic inspection method. That is, some of the optically detected defects can have a magnetic output level of a predetermined threshold value or higher. Therefore, these optically detected defects cannot be considered to be magnetically defective, though some decrease in magnetic output level is observed by the magnetic inspection. Accordingly, the optical inspection method has a problem of so-called "over-inspection".

As a result of the present inventors' earnest studies, it has been found that by first optically inspecting the surface of magnetic disc to detect defects thereon, and then precisely inspecting smaller area than the optically inspected surface and the area including the optically detected defective portions and vicinities thereof by a magnetic inspection method, the defects on and in the magnetic disc can be detected at a high speed and with a high accuracy without failed inspection and over-inspection. The present invention has been attained on the basis of the finding.

SUMMARY OF THE INVENTION

It is an object of the present invention to provide a method of inspecting a magnetic disc, which is capable of detecting defects thereon and therein at a high speed and with a high accuracy and which is free from failed detection (oversight of defects) and over-inspection.

It is another object of the present invention to provide an apparatus for inspecting a magnetic disc, which is capable of effectively performing the above-mentioned inspection method.

To accomplish the aim, in a first aspect of the present invention, there is provided a method of inspecting a magnetic disc, comprising:

optically inspecting a surface of said magnetic disc to detect defects thereon; and conducting a magnetic defect inspection to an area which is smaller than said optically inspected surface and including the optically detected defective portions and vicinities thereof.

In a second aspect of the present invention, there is provided an apparatus for inspecting a magnetic disc, comprising:

an optical head unit for conducting an optical defect inspection of the said magnetic disc; and a magnetic head unit for conducting a magnetic defect inspection of the said magnetic disc, the optical defect inspection by the said optical head unit being conducted to detect radial positions of defects on the surface of the magnetic disc, and then the optically detected radial positions of defects and vicinities thereof being magnetically inspected by the said magnetic head unit.

DETAILED DESCRIPTION OF THE INVENTION

In accordance with the present invention, the magnetic disc is first inspected to detect defects thereon by an optical defect inspection method, and then the optically detected defective portions and vicinities thereof are precisely inspected by a magnetic inspection method.

Figure 1:
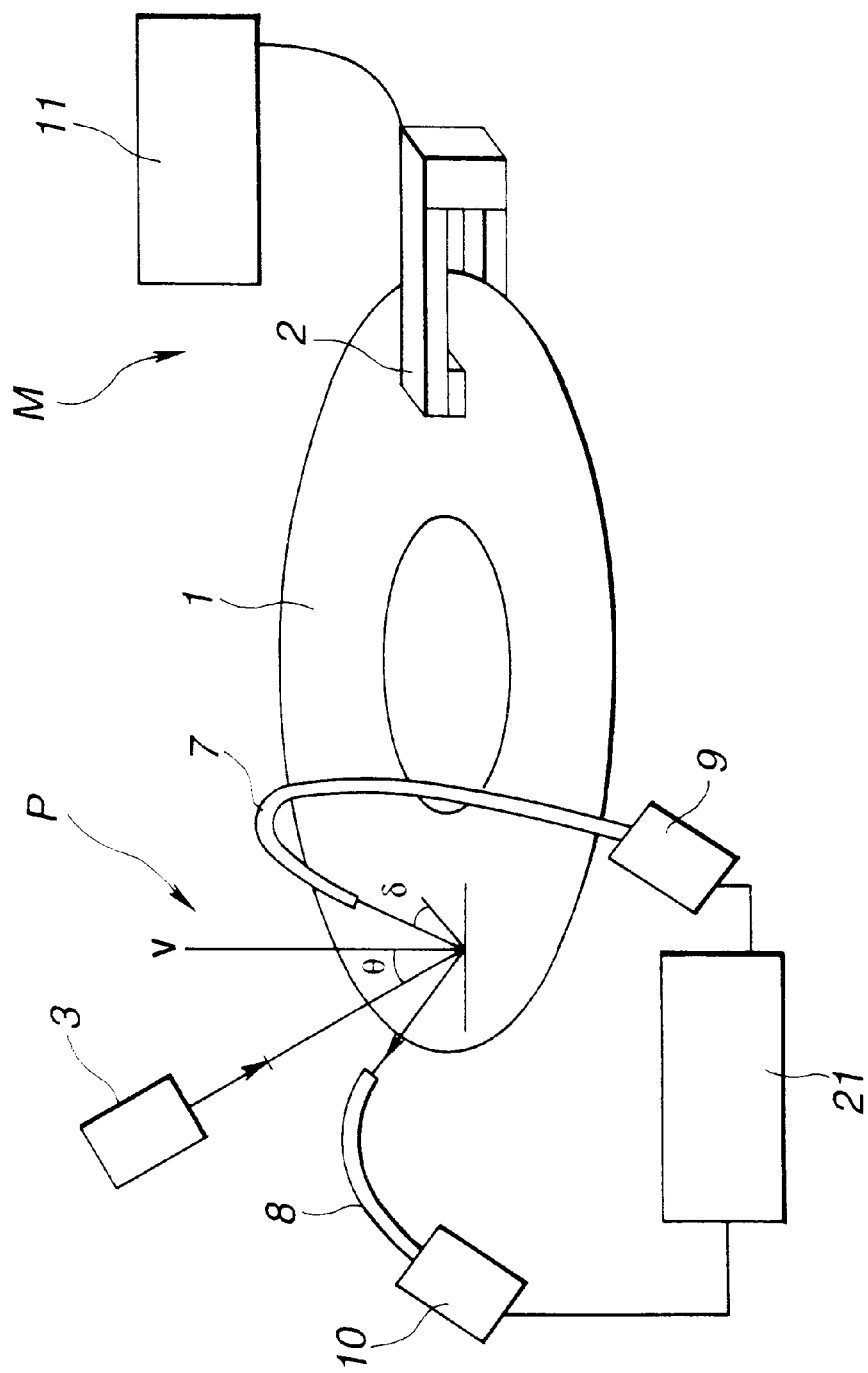
FIG. 1 is a schematic view showing an inspection apparatus according to the present invention.
Figure 2:
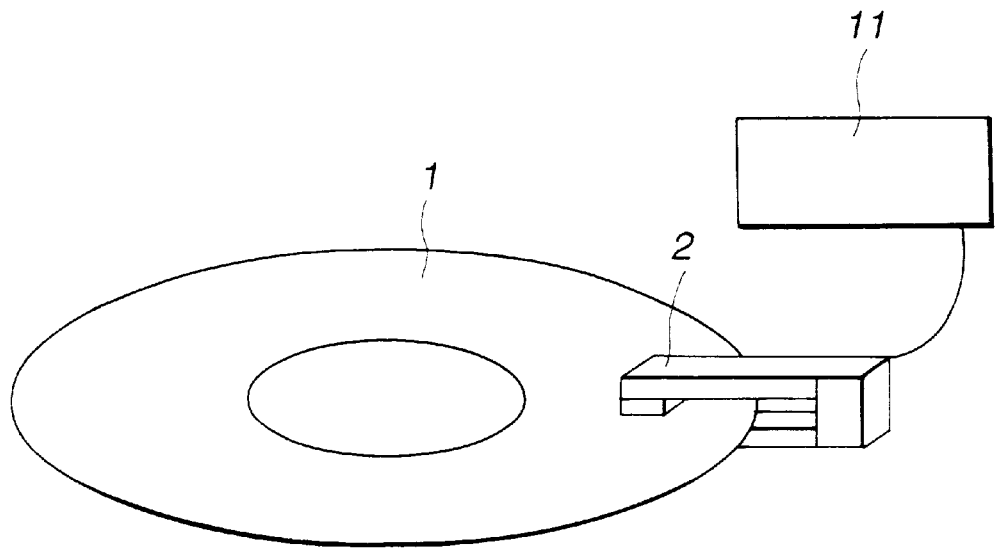
FIG. 2 is a schematic view showing a conventional magnetic defect inspection apparatus.

FIG. 1 shows an inspection apparatus applicable to the present invention. Referring to FIG. 1, the inspection apparatus comprises an optical head unit P and a magnetic head unit M, both of which are mounted on a common spindle to conduct optical and magnetic defect inspections of a magnetic disc 1 at the same time.

The optical head unit P for conducting the optical defect inspection includes a light source 3 for irradiating a light beam onto the magnetic disc 1.

As the light source 3, there can be used a laser, an incandescent lamp or the like. The light is irradiated from the light source 3 on the surface of the magnetic disc 1 in the direction inclined at an angle θ of 15 to 35 degrees relative to a normal line on a light spot thereof, and inclined at an angle of 0 to 10 degrees relative to a radial direction of the magnetic disc. It is especially preferred that an infra-red laser diode is used as the light source 3.

The light irradiated from the light source 3 is converged toward the surface of the magnetic disc 1 to form thereon a light spot having a diameter of several microns to several hundred microns. In this case, the magnetic disc 1 is moved relative to the light spot while rotating, or alternatively the light spot is moved in radial direction of the rotating magnetic disc 1, thereby enabling a whole surface of the magnetic disc 1 to be scanned and inspected.

As the light-receiving units, there can be used a photodiode, an avalanche photodiode, a photomultiplier or the like.

In the case where both of the optical head unit P as an optical defect inspection mechanism and the magnetic head unit M as a magnetic defect inspection mechanism are mounted on a common spindle, since an mounting space therefor is limited, it is preferred that the scattered lights to be received are guided through optical fibers 7 and 8 each having a lens at a tip end thereof, and then detected by light-receiving units 9 and 10, respectively. The light-receiving units 9 and 10 are connected to a signal processing unit 21.

The light-receiving unit 9 serves to receive a side low-angle scattered light and detect dusts attached onto the magnetic disc 1. A light-receiving leading portion for the light-receiving unit 9 is arranged in the direction inclined at an angle of from rearward 10 degrees to forward 30 degrees relative to the direction perpendicular to the incident light, and in the direction inclined at an angle of 0 to 10 degrees upwardly from the surface of the magnetic disc 1.

In addition, the light-receiving unit 10 serves to receive a rearward scattered light for the main purpose of detecting light-scattering caused due to scratches on the surface of the magnetic disc 1. The light-receiving leading portion for the light-receiving unit 10 is arranged in the direction inclined at an angle of ±30 degrees, preferably ±10 degrees relative to a plane of incidence of the irradiated light, and in the direction rearwardly inclined at an angle of 30 to 60 degrees, preferably 40 to 50 degrees relative to the normal line V of the magnetic disc 1.

By using the thus arranged optical head unit P, the surface of the magnetic disc is inspected in the following manner. That is, when the output of the side low-angle scattered light received by the light-receiving unit 9, is not more than a predetermined value and when the output of the rearward scattered light received by the light-receiving unit 10 exceeds a specific threshold value, it can be judged that the inspected positions are defective.

The predetermined value, that is, threshold value for the output level of the side low-angle scattered light is usually defined as the following manner. Several outputs, preferably ten outputs of side low-angle scattered lights reflected from several positions, preferably ten positions previously known as dusts were measured. The value corresponding to 50% of the smallest peak output among the thus obtained peak outputs was used as the threshold value for the output level of the side low-angle scattered light.

On the other hand, the threshold value for the output level of the rearward scattered light is usually defined as the following manner. Several outputs, preferably ten outputs of rearward scattered lights reflected from another several positions, preferably ten positions previously known as defects were measured. The value corresponding to 50% of the smallest peak output among the thus obtained peak outputs was used as the threshold value for the output level of the rearward scattered light.

The optical defect inspection can be conducted by the laser-assisted Doppler method.

In the laser-assisted Doppler method, when a laser beam is scanned while being irradiated onto the magnetic disc 1, there is caused a deviation in wavelength between the incident light and the reflected light by Doppler effect if there are any irregularities on the surface of the magnetic disc 1. By determining whether there is any deviation in wavelength between the incident and reflected lights, the defects on the magnetic disc 1 can be detected.

In the case where any defects are detected by the optical defect inspection, radial positions of the optically detected defective portions and vicinities thereof, i.e., areas having the defect as a center thereof, are precisely inspected by the magnetic defect inspection method.

The magnetic defect inspection is performed by recording a predetermined signal on the magnetic disc 1 by the magnetic head 2 having a signal processing unit 11 and then reproducing the signal therefrom, by the magnetic head 2. In the magnetic defect inspection, when a large change in reproduction output is detected, it can be judged that the positions showing such a large change in reproduction output are actual defects.

In the magnetic defect inspection, the radial regions which have been judged to include no defects by the preceding optical defect inspection, are inspected at a high speed in a track-skipping or jumping manner, while the radial positions which have been judged to include defects by the preceding optical defect inspection, are precisely inspected without the track skipping.

It is preferred that the precise magnetic defect inspection is conducted with respect to the respective regions including the radial positions of the optically detected defective portions and vicinities thereof and having a radius of 10 to 500 μm from each radial position as a center.

In the above-mentioned magnetic defect inspection, when the reproduction outputs of signals recorded at a recording density of 30 to 300 kfci are 60 to 90% of an average output level thereof and when such an output is continued for 30 to 300 microns, it can be judged that the regions inspected are defective.

Figure 3:
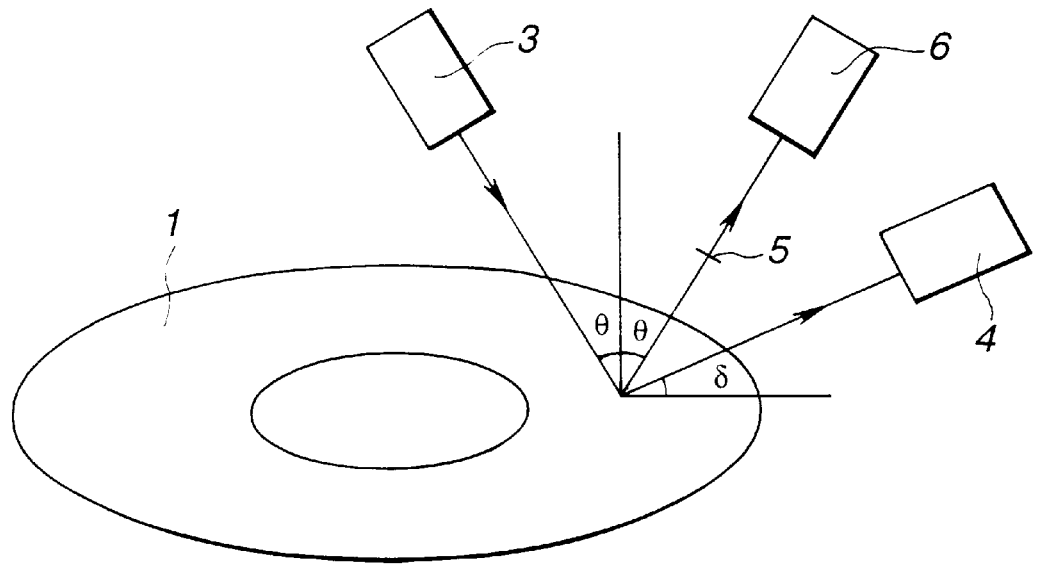
FIG. 3 is a schematic view showing a conventional optical defect inspection apparatus.

In FIG. 1, there is illustrated the inspection apparatus comprising the optical head unit P and the magnetic head unit M both of which are mounted on the common spindle. However, these units may be mounted on separate spindles. Alternatively, the optical head unit P may be replaced with such a conventional unit as shown in FIG. 3.

In this case, when the output of the low-angle scattered light received by the light-receiving unit 4 is less than the predetermined value and when the output of the mirror-reflected scattered light received by the light-receiving unit 6 exceeds the predetermined threshold value, it can be judged that the regions inspected are defective.

As the inspection methods used in the present invention, there may be exemplified a method of first conducting an optical inspection and then conducting a magnetic inspection of only the optically detected defective portions and vicinities thereof without the track skipping, while the other regions including no defects are magnetically inspected in a track skipping or jumping manner, or a method of conducting the optical and magnetic inspections successively and simultaneously.

In the case where the optical and magnetic inspections are conducted in such a simultaneous manner, the following inspection method can be used.

That is, in such an inspection method, the magnetic inspection is conducted in a track skipping or jumping manner simultaneously with the optical inspection until any defects are detected by the optical inspection. When defects are detected during the optical inspection, the optical inspection is temporarily stopped and only the magnetic inspection is conducted without track skipping or jumping.

The simultaneous inspection method has an advantage that the inspection time can be shortened. On the other hand, although the successive or stepwise inspection method in which a whole surface of the magnetic disc is first subjected to the optical inspection and then the optically detected defective portions and vicinities thereof are subjected to the magnetic inspection, requires a longer inspection time than the simultaneous inspection method, it has such an advantage in which the system thereof itself becomes simple. These inspection methods can be appropriately selected according to the requirements.

Figure 4:
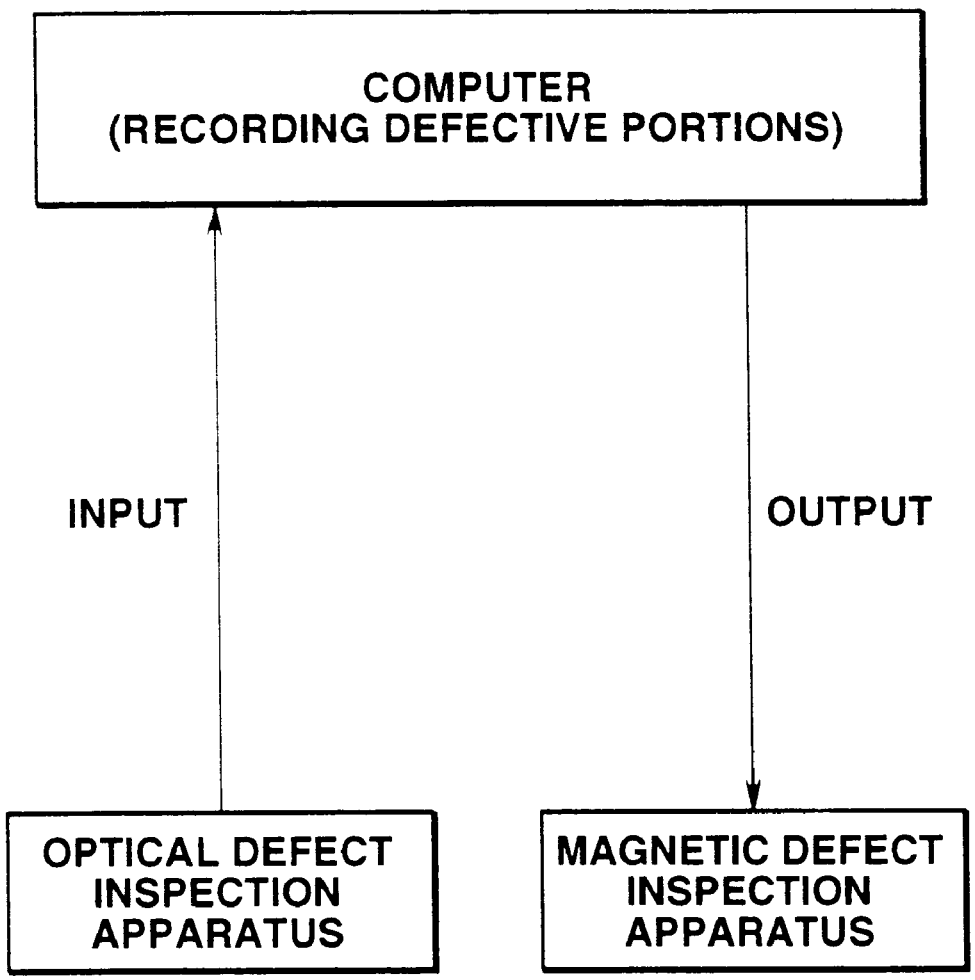
FIG. 4 is a view explaining one of inspection methods according to the present invention.

Alternatively, as shown in FIG. 4, in the case where the optical and magnetic inspections are respectively conducted by optical and magnetic inspection apparatuses mounted on separate spindles, the following inspection method can be used. That is, the results from the optical inspection are first input and recorded in a computer. Thereafter, when the magnetic inspection is conducted, the results from the preceding optical inspection of the magnetic disc which have been recorded in the computer, are output therefrom, and only the defective portions detected by the optical inspection and vicinities thereof are magnetically inspected without track skipping or jumping, while the other portions having no optically detected defects are rapidly magnetically inspected in a track skipping or jumping manner.

EXAMPLES

The present invention is described in more detail by way of examples, but these examples are only illustrative and are not intended to limit the scope of the present invention.

Example 1

A semiconductor laser capable of emitting a laser beam with a wavelength of 780 nm and having an output of 5 mW, was used as a light source of an optical defect inspection unit. A light spot formed on a surface of a magnetic disc by using the semiconductor laser was of an elliptical shape having a minor axis of 25 $\mu$m and a major axis of 120 $\mu$m. An avalanche photodiode produced by HAMAMATSU PHOTONIX CO., LTD. was used as a light-receiving element.

The incident light was controlled so as to have an incident angle of 30 degrees relative to a normal line on the surface of the magnetic disc, and to be incident on the position to be irradiated, along the radial direction of the magnetic disc. The scattered light reflected from the surface of the magnetic disc was received in the following manner. That is, two scattered lights, i.e., a rearward scattered light existing in a plane of incidence and reflected at an angle of 45 degrees relative to a normal line on the surface of the magnetic disc, and a side low-angle scattered light existing in a plane perpendicular to the plane of incidence and reflected at an angle of 5 degrees relative to the surface of the magnetic disc, were received by optical fibers each having a lens at its tip end, and guided therethrough to an avalanche photodiode as the light-receiving element.

The judgment on whether any defects were detected, was performed as follows. That is, ten outputs of rearward scattered lights reflected from 10 positions previously known as defects were measured. The value corresponding to 50% of the smallest peak output among the thus obtained peak outputs was used as a threshold value for the output level of the rearward scattered light. Whereas, ten outputs of side low-angle scattered lights reflected from another ten positions previously known as dusts were measured. The value corresponding to 50% of the smallest peak output among the thus obtained peak outputs was used as a threshold value for the output level of the side low-angle scattered light.

In addition, a threshold value for duration of the rearward scattered light output level was set to such a value that the output level of not less than the above-mentioned threshold value was continuously generated for a length of 200 $\mu$m on the magnetic disc. Further, the detection of the defects was judged in the following manner. That is, when the output level of the rearward scattered light was not less than the threshold value therefor and the generation of such an output level was continued for not less than the threshold value for the duration, and when the output of the low-angle scattered light is not more than the threshold value therefor, it was judged that the defects were detected by the optical defect inspection. Upon conducting the respective inspections, the magnetic disc was caused to rotate at 4,500 rpm. The measurement or inspection was conducted in such a manner that the surface of the magnetic disc was helically scanned by the light spot at such a scanning pitch of 50 $\mu$m as calculated in the radial direction of the magnetic disc.

In the magnetic defect inspection, an MR head having a write gap of 4 $\mu$m and a read gap of 2.5 $\mu$m was used as the magnetic head. Following the completion of the optical inspection, the portions which were judged to include no defects by the optical inspection, were magnetically inspected at a tracking pitch of 50 $\mu$m. On the other hand, with respect to the radial positions of the defects detected by the preceding optical inspection, regions including the optically detected radial positions and vicinities thereof and having a width of 100 $\mu$m relative to each radial position as a center were magnetically inspected at a tracking pitch of 2.5 $\mu$m without track skipping. In the magnetic inspection, when the reproduction output of signals recorded at a packing density of 50 kfci was not more than 80% of an average output level thereof and when such a reproduction output was continued for 200 $\mu$m, it was judged that defects were detected at the regions.

Fifty magnetic discs were magnetically inspected with respect to both surfaces thereof, and the inspection results were compared with those obtained from the magnetic inspection conducted without track skipping. In the case where the defects detected by the magnetic inspection according to the present invention were not detected as defects by the magnetic inspection without track skipping, it was considered to be "over-inspection". On the other hand, in the case where the non-defects detected by the magnetic inspection according to the present invention were detected as defects by the magnetic inspection without track skipping, it was considered to be "failed-inspection". The results were examined in terms of a percentage (%) of the number of defects involved in the "over-inspection" or those involved in the "failed inspection" to the total number of defects detected by the magnetic inspection without track skipping.

Further, the time required for the inspection per one magnetic disc was also examined in terms of a percentage (%) thereof to the time required for the magnetic inspection without track skipping. The results are shown in Table 1.

Example 2

The same procedure as defined in Example 1 was conducted using the same inspection apparatus as used in Example 1 except that a whole surface of the magnetic disc was optically inspected to determine defective positions thereon, and then positions judged to be non-defective by the optical inspection were magnetically inspected at a tracking pitch of 100 µm, while with respect to the radial positions judged to be defective by the optical inspection, regions including the radial positions and vicinities thereof and having a width of 100 µm relative to each defect as a center, were magnetically inspected at a tracking pitch of 2.5 µm without track skipping. The results are also shown in Table 1.

Comparative Example 1

The same procedure as defined in Example 2 was conducted except that the magnetic disc was magnetically inspected at a tracking pitch of 100 µm irrespective of the results of the optical inspection. The results are also shown in Table 1.

Comparative Example 2

The magnetic inspection to the all surface of the disk was only conducted without track skipping. The results are also shown in Table 1.

Comparative Example 3

The optical inspection to the all surface of the disk as defined in Example 1 was only conducted. The results are also shown in Table 1.

TABLE 1

|  | Percentage of over-inspection (%) | Percentage of failed inspection (%) | Inspection time per one disc (%) |
|---|---|---|---|
| Example 1 | 0 | 30 | 5 |
| Example 2 | 0 | 30 | 10 |
| Comparative Example 1 | 30 | 40 | 8 |
| Comparative Example 2 | 0 | 0 | 100 |
| Comparative Example 3 | 30 | 50 | 3 |

As described above, in accordance with the present invention, since circumferentially elongated defects can be detected in much closer manner to that of a magnetic inspection without track skipping as compared to conventional inspection methods, it becomes possible to shorten the inspection time without increase in percentage of over-inspected defects, thereby enhancing the productivity of magnetic discs.

What is claimed is:

1. An apparatus for inspecting a magnetic disc, comprising:

an optical head unit for conducting an optical defect inspection of said magnetic disc, said optical head unit being constituted by a mechanism configured to perform a light scattering optical inspection technique;

a magnetic head unit for conducting a magnetic defect inspection of said magnetic disc;

the optical defect inspection by said optical head unit being conducted so as to detect positions of defects on the surface of the magnetic disc with respect to a disc position reference point;

means for controlling said magnetic head unit so the optically detected positions of defects and vicinities thereof are magnetically inspected by said magnetic head unit;

wherein an incident light is incident on the magnetic disc in the direction inclined at an angle of 15 to 35 degrees relative to a normal line on the surface of the magnetic disc and inclined at an angle of 0 to 10 degrees relative to the radial direction of the magnetic disc;

wherein said optical head unit comprises a system which serves to receive a rearward scattered light resulting from reflection of the incident light on the surface of the magnetic disc, and which is arranged in the direction inclined at an angle of 0 to 30 degrees relative to a plane of incidence and inclined at an angle of 40 to 50 degrees relative to the surface of the magnetic disc, and the other system which serves to receive a side scattered light resulting from reflection of the incident light on the surface of the magnetic disc, and which is arranged in the direction inclined at an angle of from rearward 10 degrees to forward 30 degrees relative to the direction perpendicular to the plane of incidence and inclined at an angle of 0 to 10 degrees relative to the surface of the magnetic disc; and wherein when an output of the rearward scattered light received by said one system of the optical head unit is not less than a predetermined output level and when an output of the side scattered light received by said the other system of the optical head unit is not more than the predetermined output level, the optically inspected positions are judged to be defective.

2. An apparatus according to claim 1, wherein said optical head unit comprises, as a light source, an infra-red laser diode.

3. An apparatus according to claim 1, wherein the defects detected by the optical inspection are scratches elongated in the circumferential direction of the magnetic disc.

4. A method of inspecting a magnetic disc, comprising the steps of:

optically inspecting a surface of said magnetic disc to detect defects thereon;

conducting a magnetic defect inspection of a region which is smaller than the surface being optically inspected, the region including the optically detected defective portions and vicinities thereof;

wherein said conducting a magnetic defect inspection includes conducting a coarse magnetic defect inspection;

wherein said optically inspecting and said conducting a coarse magnetic inspection are performed simultaneously; and where, when said optically inspecting detects one or more defective portions, said method further includes:

stopping said optically inspecting;

conducting a precise magnetic defect inspection of the one or more optically detected defective portions and vicinities thereof; and upon completing said conducting a precise magnetic defect inspection, again simultaneously performing said optically inspecting and said conducting a coarse magnetic defect inspection.

5. A method according to claim 4, wherein by using an inspection apparatus including an optical head unit and a magnetic head unit both mounted on a common spindle, said steps of optically inspecting and conducting a magnetic inspection are successively and simultaneously conducted in such a manner that an area where the optical inspection has been completed, is successively subjected to the magnetic inspection.

6. A method according to claim 4, wherein the optical inspection is conducted by one of a light scattering optical inspection technique or a laser-assisted Doppler optical inspection technique.

7. A process for producing a magnetic disc, including a magnetic inspection step, which step comprises the steps of:

detecting regions to be subjected to said magnetic inspection step by an optical inspection; and wherein first regions for which a predetermined result is obtained by the optical inspection having conducted in advance of the magnetic inspection step, are subjected to more precise magnetic inspection than that of remaining second regions for which the predetermined result is not obtained by the optical inspection.

8. A process for producing a magnetic disc according to claim 7, wherein the magnetic disc is first inspected by the optical inspection to detect defective portions thereon and wherein the optically detected defective portions and the vicinities thereof are next inspected by said magnetic inspection step.

9. A process for producing a magnetic disc according to claim 7, wherein the optical inspection includes optically inspecting the surface of the magnetic disc to detect track positions of the defective portions and vicinities thereof; and wherein said magnetic inspection step includes conducting a precise magnetic defect inspection of the optically detected defective portions and vicinities thereof without a track skipping manner.

10. A process for producing a magnetic disc according to claim 7, wherein the optical inspection and said magnetic inspection step are successively and simultaneously conducted in such a manner that an area where the optical inspection has been completed, is successively subjected to said magnetic inspection step.

11. A process for producing a magnetic disc according to claim 7, wherein the optically detected defects are scratches elongated in the circumferential direction of the magnetic disc.

12. A process for producing a magnetic disc according to claim 7, wherein the optical inspection is conducted by one of a light scattering optical inspection technique or a laser-assisted Doppler optical inspection technique.

13. A process for producing a magnetic disc according to claim 7, wherein said magnetic inspection step includes conducting a coarse magnetic defect inspection and wherein the optical inspection and said conducting a coarse magnetic inspection are performed simultaneously.

14. A process for producing a magnetic disc according to claim 13, wherein when the optical inspection detects one or more defective portions, said method further comprises the steps of:

stopping the optical inspection;

conducting a precise magnetic defect inspection of the one or more optically detected defective portions and vicinities thereof; and upon completing said conducting a precise magnetic defect inspection, again simultaneously performing the optical inspection and said conducting a coarse magnetic defect inspection.

15. A process for producing a magnetic disc according to claim 7, wherein the optical inspection is conducted using a light scattering optical inspection technique.

16. A process for producing a magnetic disc according to claim 15, wherein the optical inspection is conducted using an infra-red laser diode as a light source.

17. A process for producing a magnetic disc according to claim 15, further comprising shining an incident light on the magnetic disc in an incident direction inclined at an angle of 15 to 35 degrees relative to a normal line on the surface of the magnetic disc and inclined at an angle of 0 to 10 degrees relative to the radial direction of the magnetic disc; and wherein the optical inspection comprises:

receiving a rearward scattered light resulting from reflection of the incident light on the surface of the magnetic disc in a first scattering direction inclined at an angle of 0 to 30 degrees relative to a plane of incidence and inclined at an angle of 40 to 50 degrees relative to the surface of the magnetic disc, receiving a side scattered light resulting from reflection of the incident light on the surface of the magnetic disc in a second scattering direction inclined at an angle of from rearward 10 degrees to forward 30 degrees relative to the direction perpendicular to the plane of incidence and inclined at an angle of 0 to 10 degrees relative to the surface of the magnetic disc, and judging the optically inspected positions to be defective when an output of the received rearward scattered light is not less than a predetermined output level and when an output of the received side scattered light is not more than the predetermined output level.

18. A process for producing a magnetic disc according to claim 7, wherein the optical inspection is conducted using a laser-assisted Doppler optical inspection technique.

19. A process for producing a magnetic disc according to claim 7, wherein the defects detected by the optical inspection are scratches elongated in the circumferential direction of the magnetic disc.

* * * * *